(12) United States Patent
Zelechonok

(10) Patent No.: US 6,893,569 B2
(45) Date of Patent: May 17, 2005

(54) METHOD AND APPARATUS FOR HIGH PRESSURE LIQUID CHROMATOGRAPHY

(75) Inventor: Yury Zelechonok, Northbrook, IL (US)

(73) Assignee: SIELC Technologies, Prospect Heights, IL (US)

( * ) Notice: Subject to any disclaimer, the term of this patent is extended or adjusted under 35 U.S.C. 154(b) by 78 days.

(21) Appl. No.: 10/462,057

(22) Filed: Jun. 16, 2003

(65) Prior Publication Data
US 2004/0251203 A1 Dec. 16, 2004

(51) Int. Cl.[7] .............................................. B01D 15/08
(52) U.S. Cl. ...................... 210/656; 210/101; 210/137; 210/143; 210/198.2
(58) Field of Search ................................. 210/635, 656, 210/659, 101, 198.2, 137, 96.1, 143; 422/70

(56) References Cited

U.S. PATENT DOCUMENTS

| 3,373,872 | A | * | 3/1968 | Jiri ........................... 210/198.2 |
| 4,116,046 | A | * | 9/1978 | Stein ........................... 73/61.55 |
| 4,840,730 | A | * | 6/1989 | Saxena ....................... 210/198.2 |
| 5,645,717 | A | * | 7/1997 | Hjerten et al. ............. 210/198.2 |
| 5,730,867 | A | * | 3/1998 | Drew et al. ................ 210/198.2 |
| 5,935,522 | A | * | 8/1999 | Swerdlow et al. ............ 422/70 |
| 6,344,172 | B1 | * | 2/2002 | Afeyan et al. ................ 422/70 |

* cited by examiner

Primary Examiner—Ernest G. Therkorn
(74) Attorney, Agent, or Firm—Charles F. Lind

(57) ABSTRACT

This modified HPLC instrument has the HPLC pump force only solvent through the serial flow line including a sampler, column, and detector; while buffer is discharged into the solvent from a syringe pump via a tee connection in the flow line downstream from the HPLC pump. A stepper motor drives the syringe pump at a discharge rate to yield an intended buffer/solvent dilution ratio compared to the steady HPLC pump flow rate. A pressure transducer detects variances of the flow line pressures, and servo controls the stepper motor for increasing the flow rate upon increased pressures and decreasing the flow rate upon decreased pressures, to hold the dilution ratio constant.

2 Claims, 4 Drawing Sheets

METHOD AND APPARATUS FOR HIGH PRESSURE LIQUID CHROMATOGRAPHY

BACKGROUND OF THE INVENTION

Some scientific and commercial applications require the continuous delivery of a secondary liquid into a flow stream of a primary liquid, where the liquid mix ratios and flow rates must remain constant. This task can be unreliable at high liquid pressures (such as between 200–10,000 psi) where liquid compressibility becomes a factor, and/or where pumping pressures might fluctuate by several percent (such as between piston pump strokes). The task can be even more challenging when the secondary to primary liquid mix ratios are highly diluted (such between 1:100 and 1:10,000).

High performance liquid chromatography (HPLC), widely used to detect and identify different components of a test sample, is commonly operated under these demanding conditions. A typical HPLC instrument is schematically illustrated in FIG. 1, including a reciprocating pump 1 serially connected by capillary lines 2, 4, 6, 8 through sampler 3, separation column 5 and detector 7, to empty into waste container 9. A computer 11 controls the operation of the HPLC instrument and can display and retain test results.

The separation column 5 is filled with a selective stationary phase (such as of powder absorbents) to provide a high mobile phase flow resistance and different mobility rates of the sample components to be analyzed. Containers 13, connected by lines 14 through a degasser 12 and a proportional valve 15 to the inlet of pump 1, hold premixed liquid solvent and buffer combinations selected for yielding specific acidic or basic properties and/or ion strengths etc. needed to react properly with the test sample.

Typical solvents might include water, methanol, acetonitrile, hexane; while typical buffers might include phosphoric acid, trifluoroacetic acid (TFA), hydrochloric acid (HCl), triethyl amine (TEA), sulfuric acid, sodium phosphate, acetic acid-triethyl amine mixture, sodium alkyl sulfate, etc.

Operation of the HPLC instrument provides that buffered solvent(s) from the containers are continuously forced by pump 1 under high pressures (up to 5,000 psi.) to flow at a constant rate (such as 100–3,000 microliters per minute) through the serially arranged downstream lines and components 2–8 and into waste container 9. Periodically, a small quantity of test sample (a few microliters) will be injected at sampler 3 into this flowing buffered solvent stream. When the sample, moving somewhat as an isolated slug within the stream, reaches the separation column 5, its components will penetrate through the stationary phase at different rates for isolated detection and identification in the detector 7.

As the buffer/solvent ratio generally is highly diluted, possibly between 1:100 and 1:10,000, each HPLC test might require very few microliters of a concentrated buffer.

The inventor has recognized significant drawbacks to premixing the buffer and solvent, storing the mixture in containers 13, and passing such buffered mixture internally through the HPLC components including the degasser 12, the proportional valve 15, pump 1, and sampler 3.

For example, the buffered solvent can crystallize on these surfaces after extended instrument nonuse or down time. The buffered solvent can also be a good media for microorganism growth and/or contamination can build up on all wetted surfaces within these components. While flushing the flow passages with solvent between consecutive tests removes most such contaminates, lingering traces cumulatively might produce background noises that hinder detector sensitivity and/or reliability.

Also, the buffered solvent generally must be manually and tediously premixed, involving weighing and/or proportioning the different solvents, buffers or other chemical ingredients needed to achieve a desired pH, etc. This procedure can be expensive considering the time and chemical costs. Further, as a buffered solvent frequently is prepared in multi-liter quantities, if it should prove to be inappropriate for a proposed test method (and is of no immediate use otherwise), it might only be disposed of as waste. The limited storage life of a buffered solvent might even dictate that it be freshly prepare immediately before an intended HPLC test.

Further complicating manual preparation of the buffered solvent, some buffers, such as trifluoroacetic acid (TFA) and triethylamine (TEA), are hazardous and require a fume hood in order to be handled. Also, corrosive buffers, such as hydrochloric acid (HCl), can be routed internally only through special HPLC instruments that cost about twice as much as a regular HPLC instrument.

SUMMARY OF THE INVENTION

An object of this invention is to provide a modified HPLC method and apparatus effective to eliminate the passage of a buffered solvent serially though all of the HPLC components, but instead to pass the buffered solvent only through the HPLC sampler, column, and detector.

A more detailed object of this invention is to provide a modified HPLC method and apparatus where the HPLC pump pressurizes only substantially pure solvent and a separate buffer pump pressurizes a concentrated buffer independently of the HPLC pump, and valving and routing lines brings these pressurized solvent and buffer liquids together downstream of many HPLC components but upstream of the sampler and column.

A broader object of the invention is to provide a method and apparatus for delivering, into a high-pressure stream of a first liquid flowing against a high resistance at a generally low steady rate, a precise amount of a second liquid, while maintaining the dilution ratio of the second/first liquids accurately constant, even at ratios up to 1:100,000 and even during pressure variations in the first liquid stream.

BRIEF DESCRIPTION OF THE DRAWINGS

These and other objects, features or advantages of the invention will be more fully understood and appreciated after considering the following description of the invention, which includes as a part thereof the accompanying drawings, wherein.

DETAILED DESCRIPTION OF THE INVENTION

Figure 1:
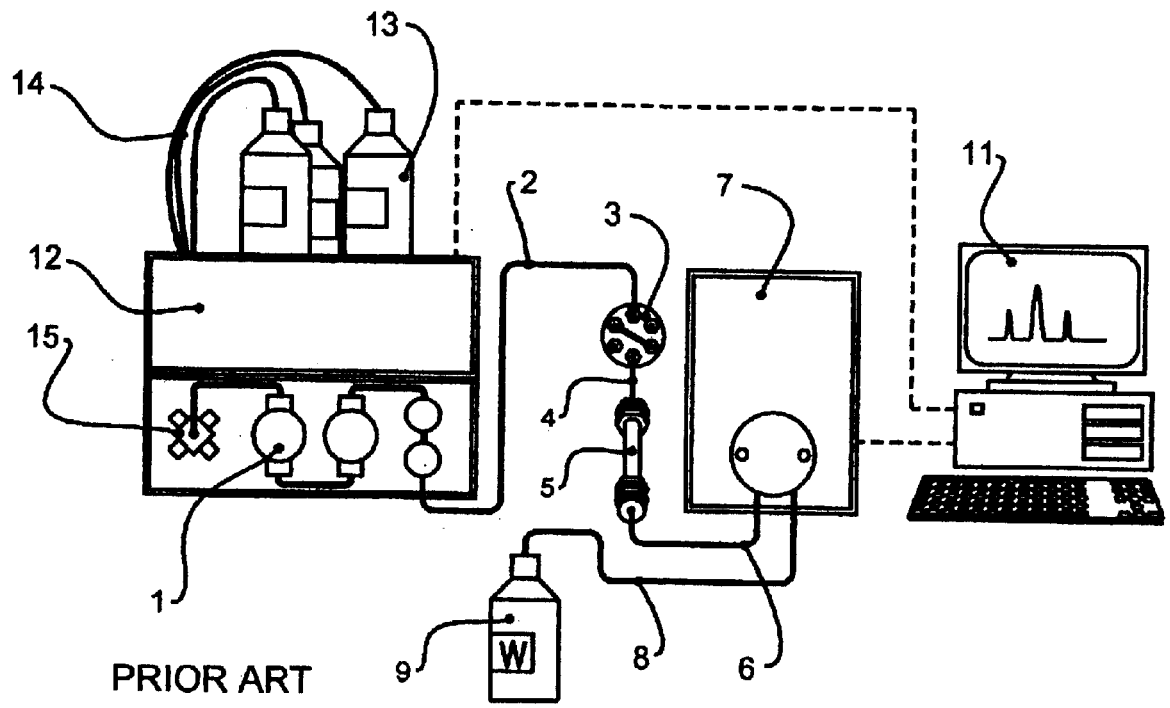
FIG. 1 is a schematic view of a conventional HPLC instrument.
Figure 2:
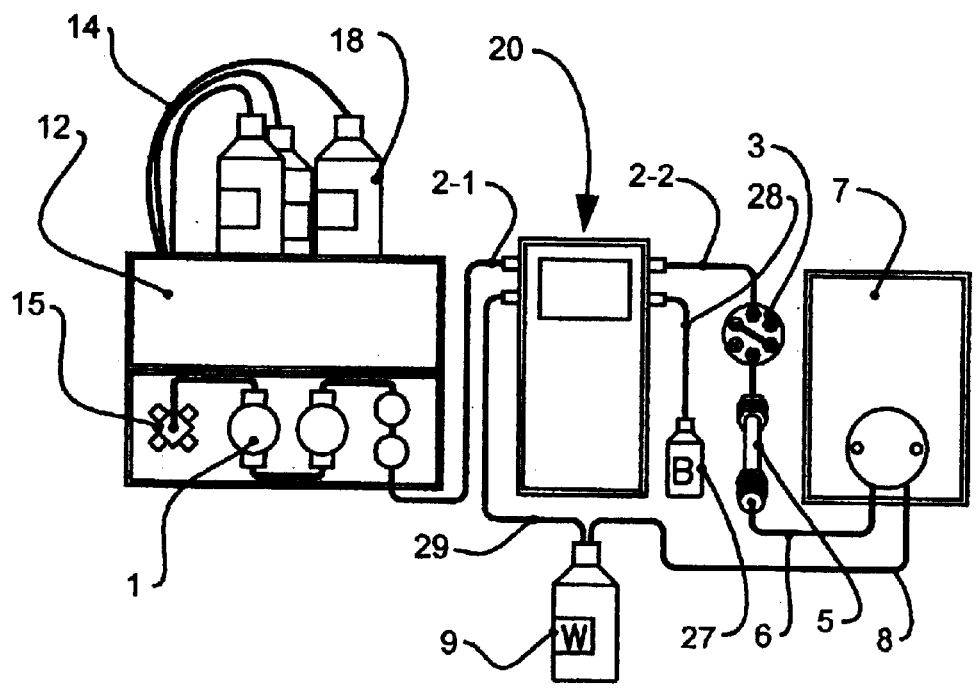
FIG. 2 is a schematic view of the improved HPLC instrument, showing where a buffer delivery apparatus to be disclosed herein can be connected.

FIG. 2 shows an improved HPLC instrument, which looks quite similar to the conventional HPLC, except that the containers 13 that conventionally held the buffered/solvent mixture are replaced by containers 18 that will hold only pure solvents. A buffer delivery apparatus 20 is also connected into the line 2 of the conventional FIG. 1 HPLC instrument, where flow lines 2—1 and 2—2 are now identified respectively upstream and downstream of the apparatus. The apparatus 20 as located is upstream of both the sampler 3 and the column 5. Further, a buffer container 27 is connected to the apparatus 20 by line 28, and the waste container 9 is connected by line 29.

Figure 3:
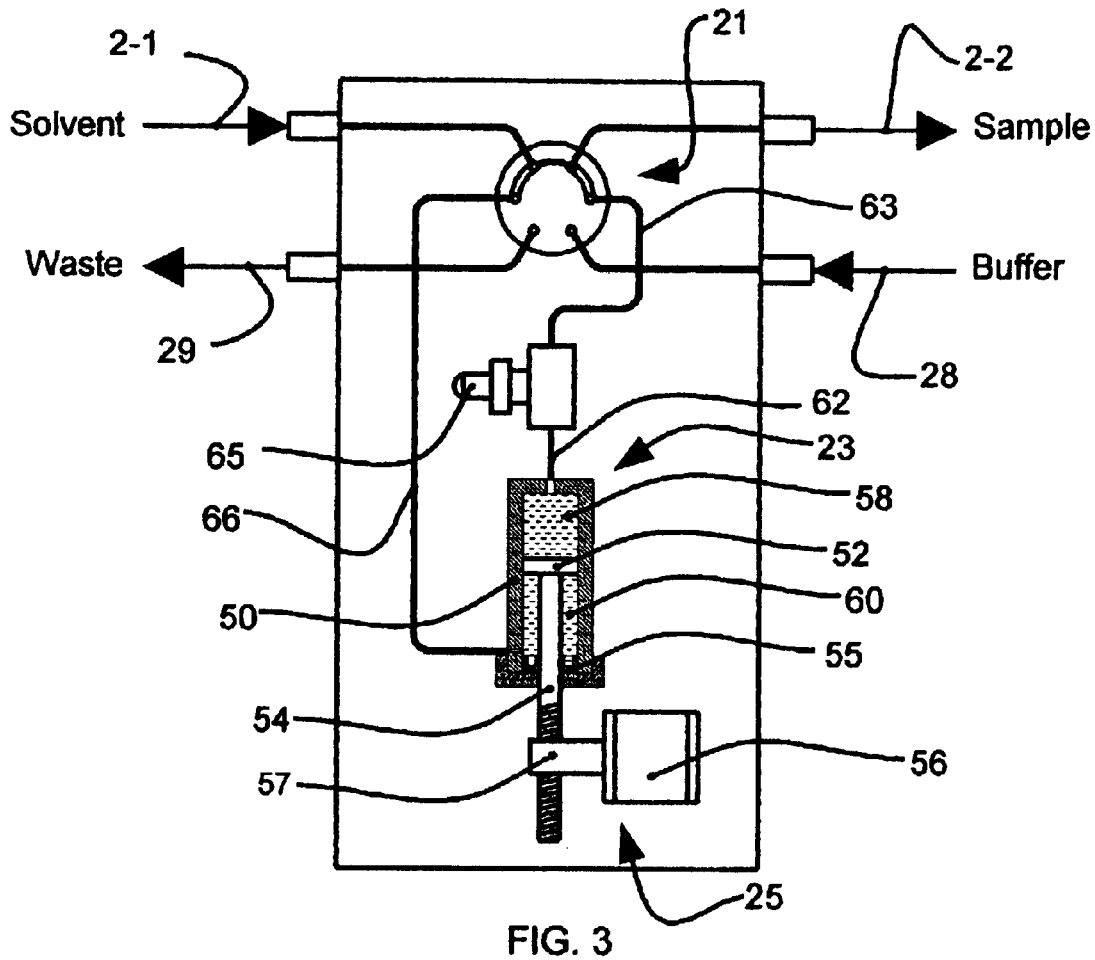
FIG. 3 is a more detailed schematic of the buffer delivery apparatus and its connections the HPLC instrument.

FIG. 3 illustrates the buffer delivery apparatus includes a valve 21, a pump 23, and a drive 25 for operating the pump in a controlled manner. Also it illustrates valve 21, with its components in the same relative position as shown in FIGS. 4A and 4B, and the flow connections between the valve, the pump 23, and the HPLC instrument components.

Figures 4A, 4B:
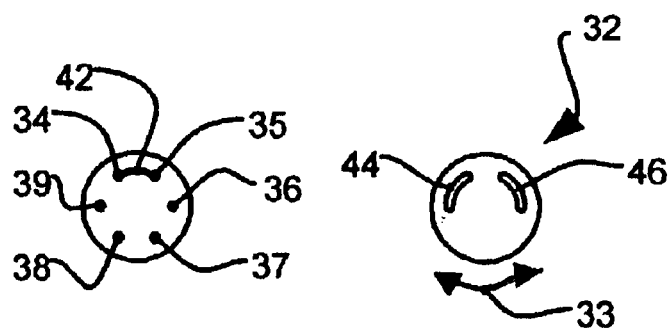
FIGS. 4A and 4B are broken away plan views of control valve components used in the buffer delivery apparatus.

Two appropriate components of the apparatus valve 21 are illustrated in greater detail in FIGS. 4A and 4B; FIG. 4A showing a stationary valve face 30 and FIG. 4B showing a movable valve member 32 that cooperatively seats on the valve face and is operatively rotated as indicated by arrow 33 between different control positions. The valve face 30 has six open ports 34, 35, 36, 37, 38 and 39 that are equally spaced apart around a circle (such as with a sixty degrees separation). The adjacent ports 34, 35 are interconnected by a capillary channel 42. The movable valve member 32 has two open channels 44, 46, separated from one another by less than a sixty degree arc and extended away from each other as arcs in excess of sixty degrees. Each channel 44, 46 will thus interconnect two and only two adjacent ports when the moveable valve member 32 is shifted to be in proper registry in its different operative positions.

The pump 23 is a single shot syringe type, having a cylinder 50 with closed ends, a piston 52 moveably seated in the cylinder 50, and a drive rod 54 connected to the piston 52 and extended through a high pressure seal 55 in one cylinder end. The piston is powered axially within the cylinder by drive 25, which can be any rotary to linear mechanism 57 driven by a reversible stepper motor 56 of good resolution. Thus, the motor in incrementally and rapidly responding to input pulses can precisely and minutely control piston movements in regards to its axial direction of movement and speed, and its exact axial position. Dual expansible chambers 58 and 60 are defined on opposite sides of the piston 52.

The main chamber 58 is connected via lines 62, 63 and a pressure transducer 65 to valve port 36, while the rod end chamber 60 is connected via line 66 to the valve port 39. The solvent line 2-1 is connected to port 34, which communicates via capillary line 42 to port 35 and via line 2—2 ultimately then to the column 5. The buffer container line 28 is connected to the port 37, while waste container line 29 is connected to the port 38.

In the operative valve position of FIG. 3, the channels 44, 46 respectively interconnect the ports 34, 39 and the ports 35, 36; meaning that the pump 1 is effectively connected to both chambers 58, 60. The chambers thus will be under substantially equal pressures (generally that of pump 1), generating almost offsetting axial mechanical forces on the piston 52 so that the piston can be shifted axially within the cylinder 50 with comparative ease.

Figure 5:
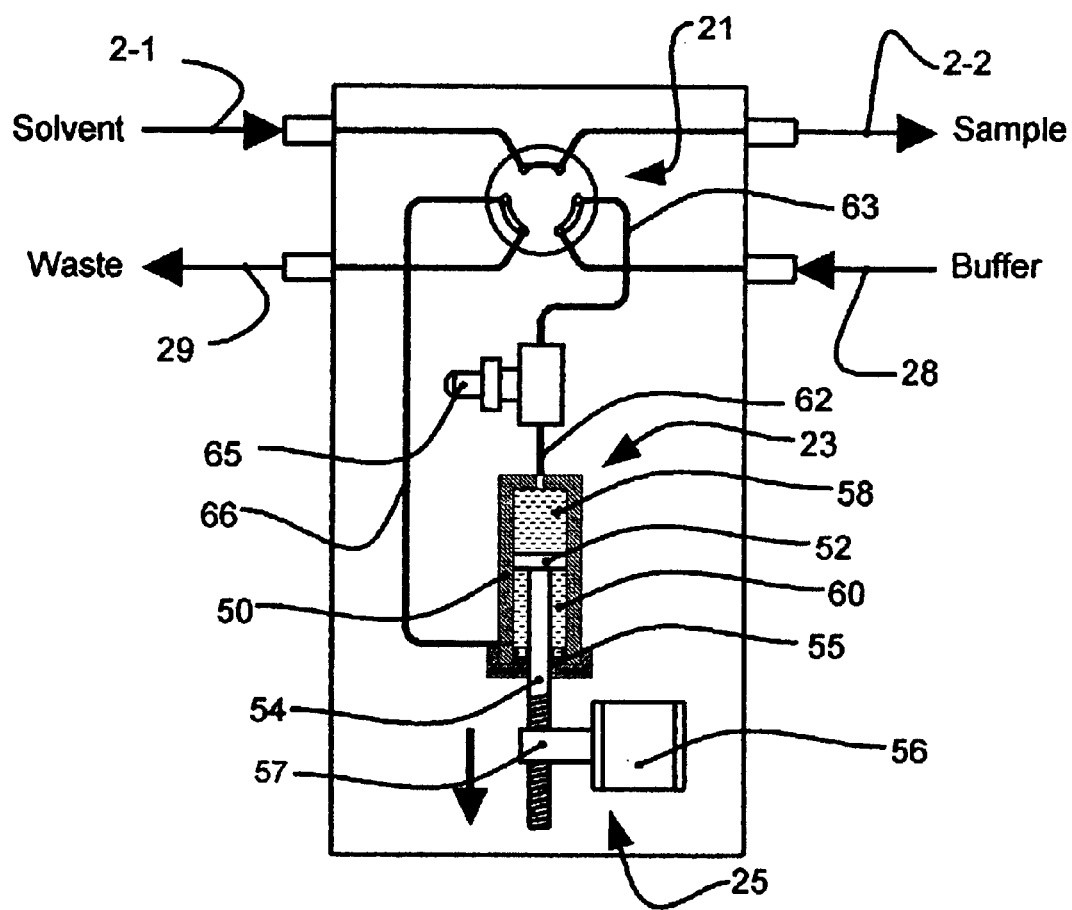
FIG. 5 is a schematic of the buffer delivery apparatus shown in an alternate operating position.
Figure 6:
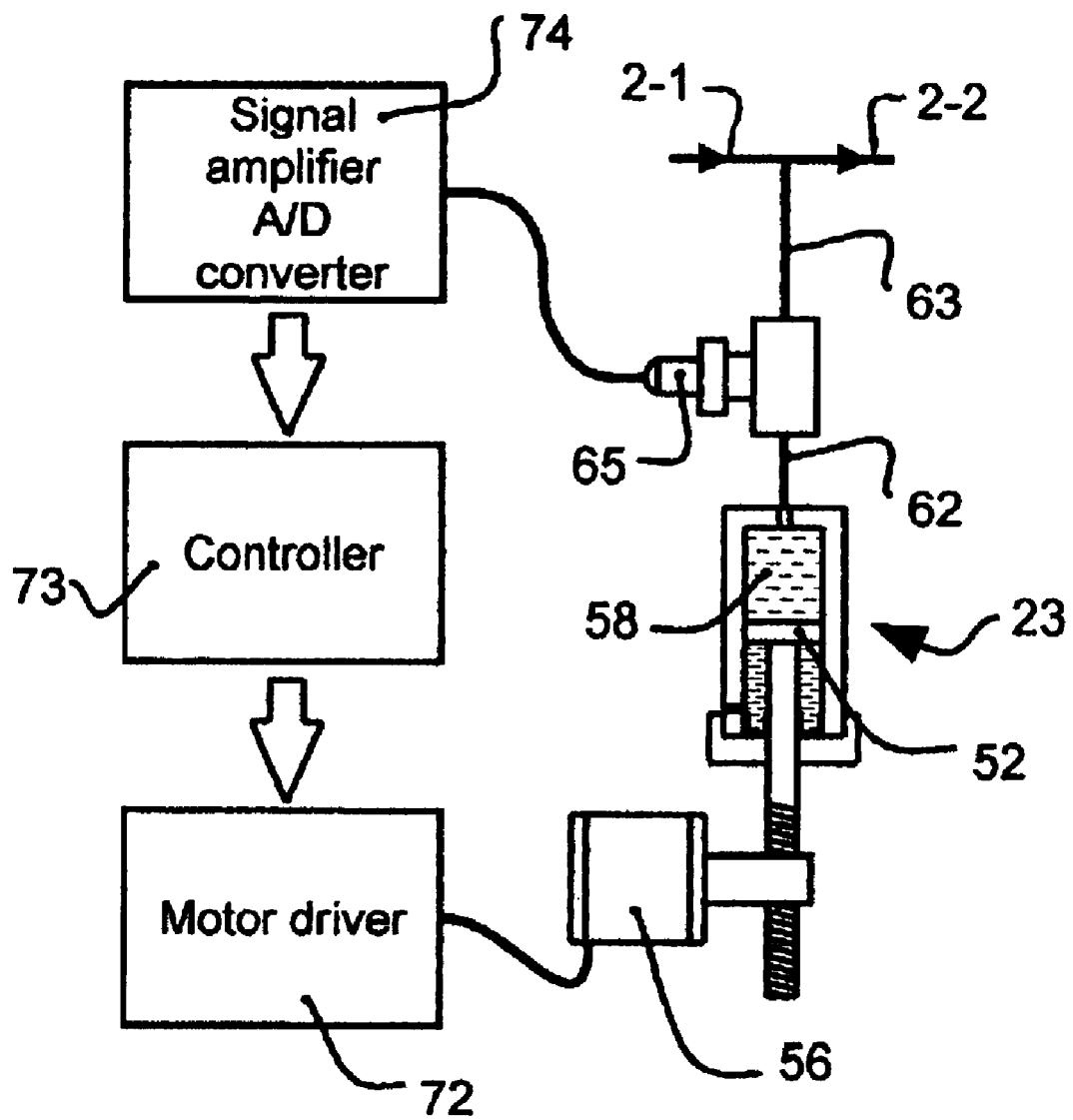
FIG. 6 is a schematic operational circuit for controlling the different operating conditions of the improved HPLC instrument.

A second operative position of the valve 21 is illustrated in FIG. 5, where the movable valve member channels 44, 46 overlie and interconnect ports 36, 37 and ports 38, 39. Thus, rod end chamber 60 is connected via line 66, connected ports 38, 39, and line 29 with the waste container 9; while main chamber 58 is connected via lines 62, 63; pressure transducer 65; connected ports 37, 36; and line 28 to the buffer container 27.

With the valve in the FIG. 5 position and the piston in the fully extended position (where main chamber 58 is of minimum volume and rod end chamber 60 is of maximum volume), retracting movement of the piston would draw buffer from the container 27 into the main chamber 58 and force the solvent in the rod end chamber 60 into the waste container 9. This buffer filling cycle would be concluded upon the piston 52 being fully retracted. In the FIG. 5 valve position, pump 1 still operatively forces the solvent via channel 42 connected ports 34, 35 to the column 5 at a substantially constant flow.

With the valve 21 shifted to the position of FIG. 3, pump 1 still would force solvent through the column 5 at the substantially constant flow, but would also pressurize the dual chambers 58, 60 and the pressure transducer 65 to substantially the same pressure.

The pressure transducer 65 responds to the solvent/buffer pressure at the lines 62, 63 and provides an analog signal proportional to this pressure. An analog to digital converter 74 converts the analog pressure detecting signal to a digital signal for transmission to the controller 73 and to motor driver 72 that generates pluses for powering the stepper motor 56 and driving the pump 23.

As the solvent flow rate via HPLC pump 1 will be substantially constant and known at line 2-1, the needed buffer piston 52 rate of advance for forcing the buffer from the chamber via the tee connection into to line 2—2 to achieve the desired buffer/solvent ratio can be calculated. The controller 73 and appropriate motor driver 72 with appropriate software can control power to the stepper motor 56 for driving the piston and achieving this rate of advance. The advancing buffer pump piston 52 will force the concentrated buffer directly into line 2—2 for mixing with the solvent therein for flow to column 5.

Should the sensed pressure increase or decrease, the noted pressure transducer 65 and servo feedback control will adjust the rate to the buffer pump motor 56, up or down, to speed it up for increased buffer flow or to slow it down for decreased buffer flow.

A sample HPLC specimen can then be injected into the flowing buffered solvent at the sampler 3, and continued operation of the pump 1 and buffer delivery apparatus 20 will force the desired ratio of mixed buffer and solvent, and specimen when added, through the column 5.

Should successive tests be needed that require different buffers, it might be desirable to flush the main chamber 58 with a suitable solvent before refilling the chamber with the new buffer. One way of doing this provides that the solvent in the rod end chamber 60 can be forced into the main chamber 58 by retracting the piston with the valve in the FIG. 4 position; and then reversing the piston movement to its extended position to force the solvent from the main chamber. Also, with the valve in the FIG. 4 position, retraction of the piston 52 will allow pump 1 to force pure solvent into the main chamber 58, while piston extension thereafter will dump the solvent out line 2—2 through the column 5. Alternatively, the buffer container 27 can be replaced with a container (not shown) of solvent and then drawing such solvent into the main chamber in the same manner as the chamber would be filled with buffer as noted above.

By way of example, the illustrated pump 23 might have a main chamber of 5,000 microliters. This would provide that with the commonly diluted ratio of buffer to solvent, one main chamber 58 full of buffer should serve a full day of testing with a typical HPLC instrument using 1 mm or 2 mm inner diameter columns. This would satisfy recent trends toward HPLC methods oriented toward the use of small bore, micro bore and short LC columns that use less solvent and run faster. All high pressure lines in the pump 23 and valve 21 should be of small cross section, such as 0.1–1.0 mm inner diameter. The maximum pressure generated by pump 23 must be approximately the same as the maximum pressure generated by pump 1.

The drive linkages 57 to the piston 52 should be accurate and highly responsive, as should be the speed controls and the high frequency pulses and rapid cycle times of the stepper motor 56. A properly operating system should compensate for small pressure changes to speed up or slow down the buffer pump 23 so as to maintain the flowing buffer/solvent mixture at the intended constant ratio.

The disclosed buffer delivery apparatus 20 and manner of operation provide accurate mixing of concentrated liquid buffer and solvent, at virtually any desired ratio, without any manual premixing, and can even change the buffer/solvent ratio on the fly merely by changing the relative rate of advance of the piston 52. The illustrated pump 23 also provides that chambers 58, 60 contain liquids at closely related pressures, so that the piston need not withstand high buffer pressures on one piston side only. Also, the cylinder seal 55 around the piston rod 54 is exposed only to solvent and not to any highly aggressive buffers.

Because of large differences between atmospheric and HPLC pump pressures, the buffer can be compressed to the extent that the buffer volume will be reduced. However, the disclosed apparatus can compensate for these volume changes. The compressibility factor "K" of the buffer commonly will be known for the ambient temperature, whereupon needed volume adjustments due to pressure change is governed by equation "I":

$$V = V_0 (1 - K\, P), \text{ where:}$$

V is the liquid volume when compressed;
$V_0$ is the starting liquid volume;
K is compressibility factor of the liquid;
P is the pressure.

Frequently the compressibility factor "K" of the buffer liquid will be known. Since buffers are usually water based substances the water compressibility factor can be used for calculation.

The actual buffer volume pumped should be the sum of the noted volume difference calculated by the compressibility equation "I" above and the stepper motor flow rate as adjusted by the pressure transducer, to achieve the desired specific buffer/solvent flow ratio. The stepper motor 56 should be adjusted repeatedly throughout the HPLC testing cycle.

The disclosed method and apparatus should increase the ease of buffer delivery but yet provide sound HPLC tests, even for applications needing low buffer/solvent ratios.

The buffer delivery apparatus 20 is shown in line 2, upstream of the sampler 3. However, it is possible to connect it instead in line 4, downstream of the sampler but upstream of the column 5. This allows the sampler 3 to be free from exposure to the buffered solvent, which might be advantageous if such were corrosive or the like.

The disclosed method and apparatus have been described in connection with an HPLC instrument, however it could prove useful in applications where a secondary liquid is to be infused into a primary liquid, at high pressures, with a resultant steady flow at a constant secondary/primary liquid dilution ratio.

While specific embodiments have been illustrated or described, changes could be made in an overall assembly without departing from the spirit of the inventive teaching. Accordingly, the invention is to be determined only by the scope of the following claims.

What is claimed as my invention is:

1. A method of operating a HPLC instrument having a constant flow rate pump, and a flow line from the pump serially through a sampler, column, and detector, the improved steps of discharging a pure liquid solvent from the HPLC pump under high pressures to provide a steady and constant flow rate through the flow line, sampler, column and detector;

separately discharging at a tee connection into the flow line between the HPLC pump and the column a concentrated buffer liquid that is at a flow rate that will provide an intended buffer/solvent dilution ratio, compared to the intended constant flow rate from the HPLC pump;

detecting any variance of the HPLC pump pressure in the flow line and responsive thereto of adjusting the rate of flow of the buffer into the line, by increasing it responsive to higher detected line pressures and decreasing it responsive to lower detected line pressures, operable toward maintaining the intended buffer/solvent dilution ratio constant.

2. A method of operating a HPLC instrument according to claim 1, further including the steps of compensating for any compressibility of the liquid buffer in having its pressure increased from atmospheric to the HPLC pump pressure, by regularly and frequently determining the decreased buffer volume with the equation:

$$V = V_0(1 - K\, P), \text{ where:}$$

V is a volume of compressed buffer,
$V_0$ is a buffer volume at atmospheric pressure,
P is the end pressure,
K is compressibility factor of the buffer; and increasing the buffer flow rate into the flow line responsive to its regularly determined decreased volume to maintain the intended buffer/solvent dilution ratio substantially constant.

* * * * *